United States Patent

Chan et al.

[11] Patent Number: 5,540,738
[45] Date of Patent: Jul. 30, 1996

[54] OXIDATIVE HAIR COLORING COMPOSITION AND PROCESS FOR DYEING HUMAN KERATINOUS FIBERS

[76] Inventors: Alexander C. Chan, 20 Jerome Ave., Mineola, N.Y. 11501; David L. Chang, 188 Flax Hill Rd., Norwalk, Conn. 06854; Yuh-Guo Pan, 119 Woodridge Dr., Stamford, Conn. 06905

[21] Appl. No.: 402,722

[22] Filed: Mar. 13, 1995

Related U.S. Application Data

[63] Continuation-in-part of Ser. No. 143,207, Oct. 26, 1993, abandoned, which is a continuation-in-part of Ser. No. 798,451, Nov. 26, 1991, abandoned.

[51] Int. Cl.$^6$ ..................................................... A61K 7/13
[52] U.S. Cl. .................. 8/406; 8/408; 8/409; 8/410; 8/411; 8/412; 8/416; 8/421; 8/423; 8/424; 8/618
[58] Field of Search .......................... 8/405, 406, 407, 8/408, 409, 423, 410, 411, 412, 416, 421, 424, 618

[56] References Cited

U.S. PATENT DOCUMENTS

| 1,677,508 | 7/1928 | Winogradoff | 8/406 |
| 4,013,404 | 3/1977 | Parent et al. | 8/405 |
| 4,888,027 | 12/1989 | Grollier et al. | 8/423 |
| 5,169,403 | 12/1992 | Chan et al. | 8/405 |

*Primary Examiner*—Douglas J. McGinty
*Assistant Examiner*—Caroline L. Dusheck
*Attorney, Agent, or Firm*—Anthony M. Santini

[57] ABSTRACT

A single-stage process for dyeing keratinous fibers in intense colors comprising simultaneously applying to said keratinous fibers a composition comprising iodide ions, an oxidant and an effective concentration of an oxidation dye to produce said intense colors when the pH of said composition is alkaline.

14 Claims, 1 Drawing Sheet

Figure 1: Plot of Intensity (L-Value) versus Dye Precursor (PPD + Resorcinol) Concentration

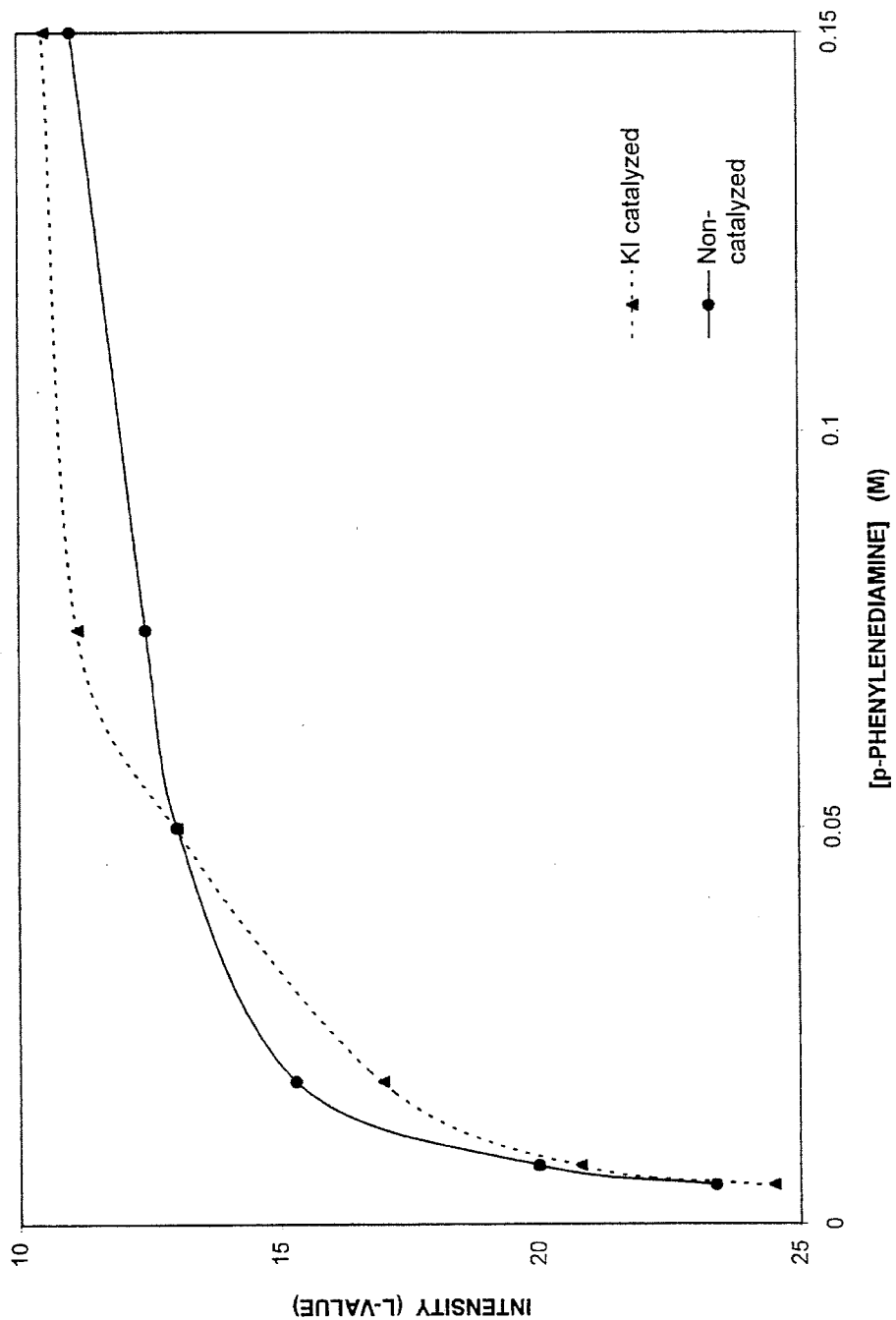

OXIDATIVE HAIR COLORING COMPOSITION AND PROCESS FOR DYEING HUMAN KERATINOUS FIBERS

This application is a continuation of application Ser. No. 08/143,207, filed Oct. 26, 1993, now abandoned, which is a continuation-in-part of application Ser. No. 07/798,451, filed Nov. 26, 1991, now abandoned.

For many years, use has been made of direct dyes, capable in themselves of coloring keratinous fibers, and oxidation dyes which, after the development of their dyeing power in an oxidizing medium, enable a coloration to be obtained which is resistant to many treatments with shampoo, to light and to inclement weather. Oxidation dyes are generally not dyes in themselves; they are intermediate compounds initially having little or no color, commonly referred to as "oxidation bases or precursors", which develop their dyeing power in, for example, hydrogen peroxide. The coloring is developed by oxidative condensation of the dye base with itself, or by oxidative condensation of the oxidation base with a compound referred to as a "coupler". A coloration of this kind is referred to as a "permanent" coloration, as opposed to the "semi-permanent" coloration obtained with direct dyes.

As the ordinary consumer is well aware, the oxidative dyeing of hair takes time. In today's day and age, time is a valuable commodity. Thus, a process which can reduce the amount of time it takes to dye hair intensely with an oxidation hair dye would be very desirable. Accordingly, the incorporation of a catalyst into a conventional two-step dyeing process was a logical development. However, the time and effort it takes to dye one's hair via a two-step process can be readily reduced via a one-step dyeing process. Unfortunately, one-step catalyst-containing processes are generally unable to produce the same intense colorings as two-step catalyst-containing processes, for reasons which will be discussed herein.

The present invention relates to, a new and improved one-step process and composition for coloring keratinous fibers, particularly hair on the human head, in very dark shades, and more particularly to an improved one-step hair coloring process and composition employing oxidation dyes comprising an oxidizing agent and iodide in an alkaline medium, wherein the final composition has a lower concentration of the dye component compared to a composition without iodide.

The prior art teaches several sequential processes for dyeing hair to intense colors using oxidation dye compositions. Although it is known to produce intense colors via sequential steps, no improved system has been discovered to produce intense colors, particularly in the dark shades, via a one-step process at high pH with significantly lower amounts of dye precursors.

German Patent DE 2028818 discloses the use of a catalyst in a pre-treatment step, prior to the application of oxidation dyes to hair. Although iodide is disclosed, the reference lists an entire array of catalysts, with no appreciation for the particular effectiveness of one catalyst over another. This patent actually relates to a controlled, sequential method of dyeing hair whereby the hair is first treated with an aqueous solution containing copper ions. Subsequently, hair is rinsed with water, and then a redox dye (such as an aromatic amine) is added. This patent lacks any criticality with respect to its pH range or catalyst. In fact, the patent states that its pH range does not matter, but preferably lies between 5 and 10. As it could span almost the entire pH range, it appears to be actually meaningless. Thus, in summary, DE 2028818 teaches a successive hair treatment with an aqueous. catalyst and dye solution to accelerate coloring on the hair, and gives no importance to the selection of a critical pH range or a critical catalyst.

British Patent 2,205,329 discloses the use of iodide ions in oxidative hair dyeing. The process involves two separate steps. The hair is first pre-treated with a mixture of oxidation dye intermediates and iodide. Then, the pre-treated hair is soaked in a hydrogen peroxide solution to complete the dyeing. Full development of the color takes place on the hair. All of the disclosed examples have a pH of the hydrogen peroxide and the dye and iodide solution in an acidic medium. Accordingly, the pH of the final composition is inherently acidic.

U.S. Pat. No. 4,985,955 discloses a sequential process for dyeing keratinous fibers with couplers combined with an iodide. There is no criticality described with respect to the pH range. It can be between two and twelve (virtually spanning the entire pH range). Additionally, no dye base is employed. This patent fails to teach the one-step process of dyeing hair to intense colors by using an oxidation dye and iodide wherein the pH of the composition must be in the alkaline range.

U.S. Pat. Nos. 4,370,142, 4,804,385, 4,808,190, and 4,888,027 all disclose iodide-containing hair dye compositions used in sequential processes for dyeing hair. None of these patents discloses a one-step process of dyeing hair using an oxidation dye/iodide-containing composition wherein the pH is maintained in the alkaline range such that the concentration of the dye intermediate can be reduced, while the production of intense colors can be maintained.

U.S. Pat. No. 5,006,127 discloses a one-step process using dye composition containing iodide in the weakly acid pH range (between 5.9 to 6.9). As is evident, this patent does not involve compositions which are alkaline. It is directed to hair coloring via acid dyeing agents. The iodide functions to accelerate the dyeing in solunion. Therefore, less dyeing takes place on the hair. This inherently results in colorings less intense than with a two-step process.

U.S. Pat. No. 1,677,508 discloses a one-step process relating to dyeing fibers of hair (but not on a living human scalp), fur, feathers and the like with vat -type dyes in an acidic environment to liberate iodine when mixed with a solution of an oxidizing agent. Although this patent relates to dyeing fibers, it is not concerned with, nor teaches anything about, dyeing hair on a human scalp in an environment which is not injurious to the scalp or hair. Moreover, the patent mentions no critical pH range. The pH concentration appears to be completely irrelevant, except when the patent talks about treating fibers with an iodine containing material "capable of liberating iodine in an acid solution of the oxidizing agent" to promote the development of dye stuff formed by oxidation upon the fibers. This patent does not disclose that the use of iodide catalysts makes possible the desired intensive coloring with alkaline dyeing agents. Thus, it has no relation to a one-step iodide-containing hair dyeing composition wherein the pH of the composition must be in the alkaline range.

The aforementioned processes of the prior art have different drawbacks insofar as they lead to either shades which are not very strong despite long exposure times, or to the production of strong shades which require a long exposure time and lead to a surface dyeing which is not very color-fast. In particular, the prior art one-step processes result in the loss of dye in solution because the addition of the oxidant to the mixing vessel begins the color development, and the presence of the catalyst accelerates such development. Thus, less dye is available to penetrate the fibers when applied to the hair. The present invention provides for greater coloring of the hair via an alkaline one-step process of applying an oxidation dye with an iodide catalyst.

OBJECTS OF THE INVENTION

Applicants have discovered that iodide ions can be used together with oxidation hair dyes in a one-step process to produce a more intense color on gray hair, especially when the pH of the composition is in the alkaline range. Thus, it is an object of this invention to provide a hair coloring mixture which provides excellent uniformly leveled and intense color throughout the hair in a one-step process.

It is another object of this invention to provide a hair coloring mixture that substantially reduces or eliminates skin discomfort during or after application in an alkaline medium.

Another object of this invention is to provide a hair coloring mixture that imparts unfading natural colors which are highly resistant to light and shampoo, even with prolonged wear and repeated shampoos.

A further object of this invention is to provide a hair coloring mixture that does not produce off-shades or streaky color sections, either during or after application thereof.

Another object of this invention is to provide a "kit" or dyeing outfit containing several compartments which employ the compounds of the present invention.

Other and more specific objects will be apparent from the features, elements, combinations and operating procedures disclosed in the following description.

SUMMARY OF THE INVENTION

Applicants have discovered that the two-step iodide-containing oxidation dye process of the prior art can actually be combined into one step to produce very intense colors with low dye concentrations and short exposure times when the pH is in the alkaline range. It is an important improvement for this kind of product if the time and materials required for dyeing can be reduced.

Ordinarily, in a two-step process, the color is entirely developed on the hair upon addition of the oxidant, thereby affording all of the developing color the opportunity to penetrate the hair fibers. The addition of a catalyst speeds up the color development on the hair.

However, in a one-step process, the oxidant is mixed with the dye precursors in a vessel where the color begins to develop in solution. Thus, less than all of the color is available for penetration into the hair fibers. The addition of a catalyst would result in even poorer coloring of the hair since the catalyst would accelerate the dye formation in solution, leaving even less dye available to penetrate the hair.

The present inventors have surprisingly discovered that the use of an iodide catalyst in a one-step oxidation dye process in an alkaline medium will produce the same or greater intensity of coloring, within the same or shorter time, with the same or lesser concentration of dye, as in a two-step process. This is particularly unexpected in view of the accelerated color development in solution normally resulting from the use of catalysts in a one-step process.

The results are even more highly surprising when one considers that dyeing hair at high pH inherently causes more bleaching of the hair than dyeing at low pH. Thus, in normal side-by-side comparisons, dyeing at low pH always has the advantage of providing greater color intensities because there is less bleaching of the hair; therefore, more base color remains. The present inventors have discovered a method by which to dye hair in one-step at high pH to produce the same or better color intensity as at low pH, without having to increase the concentration of dye to compensate for the additional bleaching effect.

The use of less dye precursors to color hair in the same intensity as with normal dye concentrations at alkaline pH not only leads to a saving in the cost of raw materials as previously mentioned, but also undoubtedly makes the products less allergenic as a result of the lower amount of dye precursors. This results in substantially improved product quality.

The process produces colorings which are both rapid and strong, and which penetrate well into the fibers, especially human keratinous fibers such as hair. The colorings have good resistance to washing and to light and become intensely colored, particularly in the dark shades, in fairly short times.

The process for dyeing keratinous fibers, preferably hair on a human scalp, according to the present invention is characterized in that a single composition containing, in a medium suitable for dyeing, dye precursors, such as p-phenylenediamine and/or m-aminophenol, iodide, such as potassium iodide, and an oxidant, such as hydrogen peroxide, is applied to the hair in one step. The pH of the composition is in the alkaline range, preferably at 9 or above. It is important to note that the composition is not preceded or followed by the oxidant but, rather, is a single, one-step formulation applied directly to the hair. Of course, application of the dyeing composition may be followed by shampooing. The iodide ion is preferably an alkali metal or alkaline earth metal or ammonium iodide, and more particularly potassium iodide. The processes implemented allow the short exposure time for the single stage process to be between 5 and 30 minutes, more preferably between 10 and 20 minutes.

The compositions used for the implementation of the process according to the present invention may be present in diverse forms, such as thickeners, creams, emulsions, foams or other forms suitable for carrying out dyeing. It is also possible to add, if required, to each of the compositions a swelling agent for the keratinous fiber such as, for example, urea. The composition may further contain additional cosmetically acceptable ingredients such as perfumes, sequestrants, film-forming agents, treatment agents, dispersants, conditioners or preservatives.

DETAILED DESCRIPTION

The composition of the present invention generally consists of a first solution comprising iodide and an oxidation dye, and a second solution comprising an oxidant in an aqueous medium. The oxidation dye consists of a dye base and dye precursors. The pH of the composition must be in the alkaline range of 8 to 14, preferably between about 9 and about 13. The process comprises mixing the first solution with the second solution immediately before application to the hair such that dyeing can take place in a single step.

The concentration range of the iodide, based on the total weight of the first solution, is 0.01–5.0%, preferably 0.05–2.0%. The concentration of the oxidation dye required under the invention is a tinctorially effective amount to produce the intense colors. The concentration range of the dye precursors, based on the total weight of the oxidation dye, is 0.01–10.0%, preferably 0.1–5.0%. The concentration range of the dye base, based on the total weight of the oxidation dye, is 90% to 99.99%, preferably 95% to 99.9%. The concentration range of the oxidant, based on the total weight of the second solution, is 1.0% to 15.0%, preferably 3.0 to 9.0%. The remaining concentration of the second solution is comprised of water and/or other of the aforementioned cosmetically acceptable ingredients. The concentration ratio of the first solution to the second solution is 1:2 to 2:1.

The dye base comprises water, ethanol, isopropanol, alkanolamines, benzylalcohol, glycerol, glycols, glycol ethers, 2-butoxyethanol, ethylene glycol, ethylene glycol monoethyl ether, propylene glycol, diethylene glycol monoethyl ether, oleic acid, surfactants, alkanolamides, ammonia, erTchorbic acid, EDTA and/or mixtures thereof.

The dye precursors comprise either at least one primary intermediate or at least one coupler, or both. The primary intermediates of the present invention consist of p-phenylenediamine, 2,5-diaminotoluene, 2,5-diaminoanisole, 2-chloro-p-phenylenediamine, N-phenyl-p-phenylenediamine, N,N-bis(2-hydroxyethyl)-p-phenylenediamine, N-(2-methoxyethyl)-p-phenylenediamine, N-furfuryl-p-phenylenediamine, 2,6-dimethyl-p-phenylenediamine, 2,3-dimethyl-p-phenylenediamine, N-methyl-p-phenylenediamine, N,N-dimethyl-p-phenylenediamine, $N^1$-ethyl-$N^1$-(2-hydroxyethyl)-p-phenylenediamine, p-aminophenol, N-methyl-p-aminophenol, 2-methyl-p-aminophenol, 3-methyl-p-aminophenol, 2,3-dimethyl-p-aminophenol, 2,6-dimethyl-p-aminophenol, 3-methoxy-p-aminophenol, 2-chloro-p-aminophenol, 2-hydroxymethyl-p-aminophenol and/or mixtures thereof.

The couplers of the present invention consist of m-aminophenol, 2-hydroxy-4-aminotoluene, 2,4-diaminophenoxyethanol, 2,4-bis(2-hydroxyethoxy)-1,5-diaminobenzene, 5-(2-hydroxyethyl)amino-2-methylphenol, 2-methoxy-5-aminophenol, 2,6-dimethyl-3-(2-hydroxyethyl)amino phenol, 3,4-methylenedioxyaniline, 2,4-dichloro-m-aminophenol, 4,6-dichloro-m-aminophenol, 1-naphthol, 1,5-dihydroxynaphthalene, 1,7-dihydroxynaphthalene, resorcinol, 2-methylresorcinol, 4-chlororesorcinol, 5-hydroxybenzodioxane, 6-hydroxybenzomorpholine, 3,3'-dihydroxydiphenylamine, 3,4-methylenedioxy-6-methoxyphenol, 4-hydroxyindole, 4-methylresorcinol, 1,3-dihydroxynaphthalene and/or mixtures thereof.

The oxidants of the present invention consist of hydrogen peroxide, perborate, urea peroxide and/or mixtures thereof.

The pH of the composition of the present invention may be maintained in the alkaline range by using pH alkalizers such as ammonia, sodium carbonate, potassium carbonate, ammonium carbonate, sodium hydroxide, potassium hydroxide, ammonium hydroxide, monoalkanolamines, dialkanolamines, trialkanolamines, alkylamines and/or mixtures thereof, and pH adjusters such as, hydrochloric acid, phosphoric acid, tartaric acid, acetic acid, oleic acid, lactic acid, citric acid and/or mixtures thereof.

As previously mentioned, it has not been heretofore known to produce the color intensities afforded by the present invention in a one-step process with relatively low dye concentrations. Applicants herein have discovered the surprising ability to produce such intense colors on hair, particularly in the dark shades, by employing an iodide catalyst in an oxidation dye composition having a pH in the alkaline range, preferably a pH of 9 or above. This is particularly surprising since iodide catalyzes the rate of reaction of the developer in solution.

Ordinarily, in a two-step process, the precursor mixture is first applied to the hair. The oxidant is subsequently added to the hair. The color is thus entirely developed on the hair upon addition of the oxidant, thereby affording all of the developing color the opportunity to penetrate the hair fibers. The addition of a catalyst would speed up the color development on the hair, without detracting from the color intensity or adversely affecting the dye concentration.

However, in a one-step process, the oxidant is first mixed with the dye precursors in a vessel prior to application to the hair. Therefore, the color begins to develop in solution in the vessel, such that less than all of the color is available for penetration into the hair fibers. In other words, a great deal of the coloring potential of the oxidation dye is lost. The addition of a catalyst would result in even poorer coloring of the hair since the catalyst would accelerate the dye formation in solution, leaving even less dye available to penetrate the hair. Accordingly, the use of a greater concentration of dye would be required, particularly with the addition of catalyst, to produce the same dyeing intensity as a two-step process.

It has been surprising to find that the addition of iodide to an oxidant and an effective concentration of dye precursors in an alkaline medium results in a one step process that enables:

A) the dyeing process to proceed at a faster rate with the same intensity of coloring and the same concentration of dye;

B) a greater intensity of coloring with the same concentration of dye and the same dyeing time;

C) the use of a lesser concentration of dye to produce the same intensity of coloring with the same dyeing time;

as in a two-step dyeing process. This is particularly unexpected in view of the accelerated color development in solution normally resulting from the use of catalysts in a one-step process.

Additionally, certain dye precursors, such as p-phenylenediamine, are suspected allergenics. Thus, by reducing the amount of the primary intermediate and/or coupler within the composition of the present invention, the composition can undoubtedly be made less allergenic to consumers, and also less costly to manufacture, while maintaining a high color intensity. The substantial reduction or elimination of skin irritation is extremely important since a painful sensation may accompany the skin irritation. To the hair dresser or user, the reduction or elimination of skin irritation is an important advantage since hair iamage is typically associated therewith. Consequently, a composition which can decrease the amount of dye precursor, yet produce intense coloring, represents a unique advancement in the hair treatment field and possesses great marketing potential.

With a view to implementing the process according to the invention, the compositions may be packaged in devices called "kits", or dyeing outfits, containing several compartments with all the components intended to be simultaneously applied to keratinous fibers by first premixing the components of the kit. Such devices may comprise, for example, a first compartment containing the composition which contains the dye precursors in the presence of iodide ions in a medium suitable for dyeing and, in a second compartment, an oxidant. In use, the components of each compartment are mixed with one another and then applied directly to the keratinous fibers in a single step operation. The final composition of the mixed compartments must maintain a pH in the alkaline range, preferably 9 or above.

According to another embodiment, the "kit" comprises a first compartment containing a composition which contains the iodide ions in a medium suitable for dyeing, a second compartment containing a composition which contains the dye precursors in a medium suitable for dyeing, and a third compartment containing 1–40 volume oxidant composition, the compositions contained in the three compartments being intended to be mixed with one another simultaneously at the time of use. The final composition of the mixed compartments will have a pH in the alkaline range, preferably 9 or above.

The devices may be equipped with means for mixing at the time of use which are known in themselves and which may be packaged in an inert atmosphere.

The process according to the invention and the corresponding compositions may be used for dyeing natural or already dyed hair, permed or uncurled, or strongly or slightly bleached hair.

It is also possible to use the above for dyeing furs or wool.

The following examples are intended to illustrate the invention without implied limitation.

EXAMPLE 1

The following example illustrates a series of hair dyeing experiments using p-phenylenediamine dihydrochloride and 5-amino-o-cresol as dye precursors. Table 1 clearly sets forth the advantage of the present invention over the use of one-step non-iodide-containing oxidation dye compositions, and over the two-step iodide-containing oxidation dyeing process, as well as over the one-step iodide-containing oxidation dye compositions at low pH.

Human hair tresses were treated with solution (A) and solution (B) for 30 min. followed by shampooing. In the case of solution (C), after 20 min. of treatment, and without intermediate rinsing, a solution of 9% $H_2O_2$ at pH 3 was then applied for an additional 10 min. before shampooing. The results indicate that the non-iodide-containing one-step method (solution A) gives the weakest color. The two-step iodide-containing method affords an intermediate intensity at alkaline pH (solution C). The most intense dark color was obtained by the one-step iodide-containing process of the present invention at alkaline pH (solution B). It is noteworthy to point out that the color obtained from solution B is also more red and brighter than that from either A or C.

Solution A (No Iodide):

| p-Phenylenediamine dihydrochloride | 0.18% |
| 5-Amino-o-cresol | 0.13% |
| Ethyl alcohol | 15.0% |
| Water qs | 100 g |

Ammonium hydroxide solution is used to adjust the pH to 9. One part of this solution is mixed with 0.5 part of 9% $H_2O_2$ and then applied to hair for 30 min.

Solution B (Iodide/One-Step):

| p-Phenylenediamine dihydrochloride | 0.18% |
| 5-Amino-o-cresol | 0.13% |
| Potassium iodide | 0.17% |
| Ethyl alcohol | 15.0% |
| Water qs | 100 g |

Ammonium hydroxide solution is used to adjust the pH to 5 or 9. One part of this solution is mixed with 0.5 part of 9% $H_2O_2$ and then applied to hair for 30 min.

Solution C (Iodide/2-Step):

| p-Phenylenediamine dihydrochloride | 0.18% |
| 5-Amino-o-cresol | 0.13% |
| Potassium iodide | 0.17% |
| Ethyl alcohol | 15.0% |
| Water qs | 100 g |

Ammonium hydroxide solution is used to adjust the pH to 5 or 9. One part of this solution is applied to hair for 20 min. and, without intermediate rinsing, a solution of 9% $H_2O_2$ at pH 3 is then applied for an additional 10 min. before shampooing. Total treatment time is 30 minutes.

TABLE 1

TRISTIMULUS VALUES OF HAIR DYED BY DIFFERENT PROCEDURES AT DIFFERENT pH'S

| Solution | pH | L | a | b |
| --- | --- | --- | --- | --- |
| A | 9 | 20.4 | 6.4 | 1.8 |
| B | 5 | 18.1 | 5.2 | 1.3 |
| B | 9 | 14.3 | 7.4 | −0.1 |
| C | 5 | 18.0 | 5.7 | 1.8 |
| C | 9 | 17.8 | 5.7 | 1.3 |

The darkest color is obtained by the one-step iodide-containing method of the present invention at alkaline pH Solution B).

TABLE 1 clearly shows that a one-step iodide-containing process at high pH is superior to:

1) A one-step non-iodide-containing process at high pH;
2) A one-step iodide-containing process at low pH;
3) A two-step iodide-containing process at low pH; and
4) A two-step iodide-containing process at high pH.

EXAMPLE II

In each case below, the dye composition contained 0.038M of p-phenylenediamine with equimolar m-aminophenol as the dye precursors in a water/ethyl alcohol (4:1) mixture. A blended gray hair tress was used in each run. When KI was desired, 15 mg of the solid was used.

The present invention applied a mixture of 5 g of the above dye composition, 15 mg of KI, and 5 g of 6% $H_2O_2$ to hair in one step at pH 9.5 for 20 min.

in an iodide pretreatment method, the hair was kept in a 5 g solution of KI for 5 min. The fiber was rinsed and treated with a mixture of 5 g of the above composition and 5 g of 6% $H_2O_2$ at pH 9.5 for 15 min.

Tristimulus values of the dyed swatches are recorded in Table 2. It is evident that the one-step process of the present invention gives the most intense color on hair as indicated by the L-value. The one-step process also affords the most violet shade (smaller b value indicates the color is more blue), while the iodide pretreatment method produces a yellowish brown color on hair as indicated by a larger b (more yellow) value.

TABLE 2

COMPARISON OF DIFFERENT HAIR DYEING PROCESSES CATALYZED BY IODIDE

| Method | L | a | b |
| --- | --- | --- | --- |
| Present Invention | 11.1 | 2.0 | 0.8 |
| I-pretreatment | 13.9 | 2.0 | 1.8 |

TABLE 2 clearly shows that a one-step iodide-containing process at high pH is superior to an iodide-pretreatment process at high pH.

EXAMPLE III

FIG. 1 illustrates a series of hair dyeing experiments using p-phenylenediamine and resorcinol as dye precursors. The amount of iodide was constant in each run (16 mg), but the concentration of dye precursors was varied. It is interesting to find that a certain dye precursor concentration must be satisfied before the catalytic effect can be observed. For instance, once an effective concentration (in this case, 0.05M) was reached, less dye was required to produce the same color intensity as the non-catalyzed composition. Conversely, when the iodide-catalyzed composition is compared to the non-catalyzed composition at equal dye concentrations, the iodide-catalyzed composition produces more intense colorings after the effective dye concentration has been reached. It is truly unexpected that more intense dye colorings can be produced by reducing the amount of dye in the composition.

EXAMPLE IV

The following example illustrates the use of p-aminophenol and m-phenylenediamine as the dye precursors mixed with equal part of 6% hydrogen peroxide and potassium iodide. The mixture was applied in one-step to blended gray hair after the pH was adjusted to 9.0 with ammonium hydroxide:

| | |
| --- | --- |
| p-Aminophenol | 0.16% |
| m-Phenylenediamine | 0.16% |
| Ethyl alcohol | 15.0% |
| Potassium iodide | 0.06% |
| Water q.s. | 100.0% |

After 20 min., a reddish brown color was imparted on hair after shampooing and rinsing. In the control experiment, no iodide was used and the color was much weaker, as indicated in the following TABLE 3:

| | L | a | b |
| --- | --- | --- | --- |
| Control | 22.2 | 2.3 | 5.4 |
| with KI | 15.8 | 5.4 | 2.4 |

EXAMPLE V

The following composition was prepared in the same manner as Example IV, except different precursors and catalysts were used.

| | |
| --- | --- |
| 4,6-Bis-(2-hydroxyethoxy) 1,3-diaminobenzene dihydrochloride | 0.60% |
| 2,5-Diaminotoluene sulfate | 0.44% |
| Ethyl alcohol | 10.0% |
| Sodium iodide | 0.27% |
| Water q.s. | 100.0% |

This composition was mixed with equal part of 6% hydrogen peroxide. The pH of this mixture was adjusted to 9.0 with ammonium hydroxide and was then used in one-step to treat blended gray hair for 20 min. No iodide was used in the control. The result illustrates that iodide enhances the dyeing efficiency of the dye composition, when it would otherwise be expected to accelerate the rate of color development in solution, leaving less color for application to the hair.

TABLE 4

| | L | a | b |
| --- | --- | --- | --- |
| Control | 15.3 | 0.4 | −0.9 |
| with NaI | 14.5 | 0.8 | −1.4 |

EXAMPLE VI

Blended gray hair was dyed by a mixture of equal part of Nice & Easy* Shade 124 and peroxide in one-step in an alkaline medium or 20 minutes. The result was compared to those swatches dyed for 15 min. by the same solution containing 0.15% of either copper sulfate or potassium iodide. Tristimulus values of the swatches are given below:
*Trademark—Clairol, Inc.

TABLE 5

COMPARISON OF DIFFERENT CATALYSTS

| Catalyst | L | a | b |
| --- | --- | --- | --- |
| none | 10.4 | 0.6 | 0.6 |
| CuSO$_4$ | 11.0 | 0.8 | 1.0 |
| KI | 9.6 | 0.5 | 0.3 |

It is evident that, when the copper sulfate catalyst was used, a lower color intensity was obtained on the hair as compared to no catalyst at all. This is to be expected since catalysts accelerate the development of the color in solution, leaving less color available to dye the hair. However, it is very surprising to find that iodide enables intense dyeing of the hair, notwithstanding its normally expected rate of catalysis of the dyeing solution. The dye-out is even more intense than when no catalyst is used at all.

EXAMPLE VII

TABLE 6

TRISTIMULUS VALUES OF BLENDED GRAY HAIR DYED WITH NICE 'N EASY* (NNE) HAIR DYES

| No. | Dye Composition | L | a | b |
| --- | --- | --- | --- | --- |
| 1 | NNE 122 (original) + H$_2$O$_2$ | 9.8 | 0.5 | 1.4 |
| 2 | NNE 122 (⅓ diluted) + H$_2$O$_2$ | 14.3 | 1.3 | 3.1 |
| 3 | NNE 122 (⅓ diluted) + H$_2$O$_2$ + KI | 10.2 | 1.8 | 1.0 |
| 4 | NNE 122 (⅓ diluted) + KI, followed by H$_2$O$_2$ | 11.3 | 2.2 | 1.0 |
| 5 | NNE 124 (original) + H$_2$O$_2$ | 9.2 | 0.0 | 1.2 |
| 6 | NNE 124 (⅓ diluted) + H$_2$O$_2$ | 11.4 | 1.0 | 1.6 |
| 7 | NNE 124 (⅓ diluted) + H$_2$O$_2$ + KI | 8.3 | 2.2 | 0.6 |

TABLE 6-continued

TRISTIMULUS VALUES OF BLENDED GRAY HAIR
DYED WITH NICE 'N EASY* (NNE) HAIR DYES

| No. | Dye Composition | L | a | b |
| --- | --- | --- | --- | --- |
| 8 | NNE 124 (⅓ diluted) + H₂O₂ + NaI | 9.0 | 0.1 | 0.9 |

Table 6 sets forth comparative data using Nice 'N Easy* 122 and 124 dye compositions at a pH of 9.5. Resorcinol, m-aminophenol and p-phenylenediamine are used as the dye precursors. Sample No. 1 represents the original 122 dye composition color intensity. This is the intensity standard against which the present invention is measured. Sample No. 2 represents the 122 dye composition diluted to one-fifth of its original dye concentration and tested again for color intensity to measure the loss of color. Sample No. 3 represents the present invention wherein 0.15% of potassium iodide is added to the diluted 122 compositions for application in a single stage. A black color very close to the original dye intensity was obtained, with iodide and an effective concentration of only one-fifth the amount of dye. It is surprising that such intense coloring can be obtained by a one-stage iodide/peroxide developer system at an alkaline pH with a lower dye concentration. Sample No. 4 represents the composition of Sample No. 3 applied in a two-stage process. As is evident, the two-stage process produces a much lower color intensity than the one-stage process, and produces a significantly lower color intensity than the original, undiluted composition.

*Trademark—Clairol, Inc.

Similarly, Sample No. 5 represents the original 124 dye composition color intensity. Sample No. 6 represents the 124 dye composition diluted to one-third of its original dye concentration and tested again for color intensity to measure the loss of color. Samples No. 7 and 8 represent the present invention wherein 0.21% of the iodide salt was added to the diluted 124 composition for application in a single stage. It is highly surprising to find that colors even more intense than the original composition can be produced by a composition having iodide and an effective concentration of one-third the dye concentration of the original composition. This results from the one-stage iodide/peroxide developer system of the present invention when the pH is alkaline.

EXAMPLE VIII

As shown in the preceding Example VII, an advantage of incorporating iodide into a one-step alkaline oxidation dye composition is to provide for a significant reduction in the dye precursor concentration to produce the same, or greater, dye-out as a non-iodide catalyzed oxidation dye composition. However, the present invention makes it also possible to reduce the amount of time required to dye hair with the same dye concentration and color intensity as non-iodide catalyzed oxidation dye compositions. This is exemplified below:

A swatch of blended gray hair was dyed in one step in an alkaline medium with a mixture of equal part of Nice & Easy* Shade 124 and hydrogen peroxide for 20 min. This was compared to swatches dyed by the same solution also containing 0.15% iodide. The results suggest that as much as 50% of the dyeing time can be reduced by incorporating iodide into the dye formulation.

*Trademark—Clairol, Inc.

TABLE 7

COMPARISON OF DYEING TIME VS. CATALYST
CONCENTRATION

| Dyeing time (min.) | KI (%) | L | a | b |
| --- | --- | --- | --- | --- |
| 20 | 0 | 10.4 | 0.6 | 0.6 |
| 15 | 0.15 | 9.6 | 0.5 | 0.3 |
| 10 | 0.15 | 10.4 | 0.8 | 0.6 |
| 5 | 0.15 | 12.7 | 1.2 | 1.3 |

It will thus be seen that the objects set forth above, among those made apparent from the preceding description, are efficiently attained and, since certain changes may be made without departing from the scope of the invention, it is intended that all matter contained in the above description shall be interpreted as illustrative so as to obtain the benefit of all equivalents to which the invention is fairly entitled.

It is also to be understood that the following claims are intended to cover all of the generic and specific features of the invention herein described, and all statements of the scope of the invention which, as a matter of language, might be said to fall therebetween.

What we claim is:

1. A single application process for dyeing keratinous fibers comprising applying to said fibers a single composition of a mixture of a first solution and a second solution, said first solution comprising (a) iodide present in an amount ranging from about 0.01% to about 5.0%, based on the total weight of said first solution, wherein the iodide is selected from ions of the group consisting of alkali metals, alkaline earth metals and ammonium; and (b) a tinctorially effective concentration of an oxidation dye comprising a dye precursor selected from the group consisting of p-phenylenediamine, 2,5-diaminotoluene, 2,5-diaminoanisole, 2-chloro-p-phenylenediamine, N-phenyl-p-phenylenediamine, N,N-bis(2-hydroxyethyl)-p-phenylenediamine, N-(2-methoxyethyl)-p-phenylenediamine, N-furfuryl-p-phenylenediamine, 2,6-dimethyl-p-phenylenediamine, 2,3-dimethyl-p-phenylenediamine, N-methyl-p-phenylenediamine, N-N-dimethyl-p-phenylenediamine, $N^1$-ethyl-$N^1$-(2-hydroxyethyl)-p-pheneylenediamine, p-aminophenol, N-methyl-p-aminophenol, 2-methyl-p-aminophenol, 3-methyl-p-aminophenol, 2,3-dimethyl-p-aminophenol, 2,6-dimethyl-p-aminophenol, 3-methoxy-p-aminophenol, 2-chloro-p-aminophenol, 2-hydroxymethyl-p-aminophenol, m-aminophenol, 2-hydroxy-4-aminotoluene, 2,4-diaminophenoxyethanol, 2,4-bis(2-hydroxyethoxy)-1,5-diaminobenzene, 5-(2-hydroxyethyl)amino-2-methylphenol, 2-methoxy-5-aminophenol, 2,6-dimethyl-3-(2-hydroxyethyl)aminophenol, 3,4-methylenedioxyan iline, 2,4-dichloro-m-aminophenol, 4,6-dichloro-m-aminophenol, 1-naphthol, 1,5-dihydroxynaphthalene, 1,7-dihydroxynaphthalene, resorcinol, 2-methylresorcinol, 4-chlororesorcinol, 5-hydroxybenzodioxane, 6-hydroxybenzomorpholine, 3,3'-dihydroxydiphenylamine, 3,4-methylenedioxy-6-methoxyphenol, 4-hydroxyindole, 4-methylresorcinol, 1,3-dihydroxynaphthalene and mixtures thereof; said second solution comprising about 1.0% to about 15.0% of an oxidant, based on the total weight of said second solution, in an aqueous medium; wherein the concentration ratio of said first solution to said second solution is from about 1:2 to about 2:1; and wherein the pH of said single composition is alkaline.

2. The process of claim 1 wherein the pH is from about 9 to about 13.

3. The process of claim 2 wherein the oxidant is selected from the group consisting of hydrogen peroxide, persulfate, perborate, urea peroxide and/or mixtures thereof.

4. The process of claim 2 wherein the iodide is potassium iodide.

5. The process of claim 2 wherein the oxidation dye further comprises, based on the total weight of the oxidation dye, about 90% to about 99.99% of a dye base and about 0.01% to about 10.0% of said dye precursor.

6. The process of claim 5 wherein the dye base is selected from the group consisting of water, ethanol, isopropanol, alkanolamines, benzylalcohol, glycerol, glycols, glycol ethers, 2-butoxyethanol, ethylene glycol, ethylene glycol monoethyl ether, propylene glycol, diethylene glycol monoethyl ether, oleic acid, surfactants, alkanolamides, ammonia, erythorbic acid, EDTA and/or mixtures thereof.

7. The process of claim 1 wherein the keratinous fibers are human hairs.

8. A single composition for dyeing keratinous fibers comprising a mixture of a first solution and a second solution, said first solution comprising (a) iodide present in an amount ranging from about 0.01% to about 5.0%, based on the total weight of said first solution, wherein the iodide is selected from ions of the group consisting of alkali metals, alkaline earth metals and ammonium; and (b) a tinctorially effective concentration of an oxidation dye comprising a dye precursor selected from the group consisting of p-phenylenediamine, 2,5-diaminotoluene, 2,5-diaminoanisole, 2-chloro-p-phenylenediamine, N-phenyl-p-phenylenediamine, N,N-bis(2-hydroxyethyl)-p-phenylenediamine, N-(2-methoxyethyl)-p-phenylenediamine, N-furfuryl-p-phenylenediamine, 2,6-dimethyl-p-phenylenediamine, 2,3-dimethyl-p-phenylenediamine, N-methyl-p-phenylenediamine, N-N-dimethyl-p-phenylenediamine, $N^1$-ethyl-$N^1$-(2-hydroxyethyl)-p-pheneylenediamine, p-aminophenol, N-methyl-p-aminophenol, 2-methyl-p-aminophenol, 3-methyl-p-aminophenol, 2,3-dimethyl-p-aminophenol, 2,6-dimethyl-p-aminophenol, 3-methoxy-p-aminophenol, 2-chloro-p-aminophenol, 2-hydroxymethyl-p-aminophenol, m-aminophenol, 2-hydroxy-4-aminotoluene, 2,4-diaminophenoxyethanol, 2,4-bis(2-hydroxyethoxy)-1,5-diaminobenzene, 5-(2-hydroxyethyl)amino-2-methylphenol, 2-methoxy-5-aminophenol, 2,6-dimethyl-3-(2-hydroxyethyl)amino phenol, 3,4-methylenedioxyaniline, 2,4-dichloro-m-aminophenol, 4,6-dichloro-m-aminophenol, 1-naphthol, 1,5-dihydroxynaphthalene, 1,7-dihydroxynaphthalene, resorcinol, 2-methylresorcinol, 4-chlororesorcinol, 5-hydroxybenzodioxane, 6-hydroxybenzomorpholine, 3,3'-dihydroxydiphenylamine, 3,4-methylenedioxy-6-methoxyphenol, 4-hydroxyindole, 4-methylresorcinol, 1,3-dihydroxynaphthalene and mixtures thereof; said second solution comprising about 1.0% to about 15.0% of an oxidant, based on the total weight of said second solution, in an aqueous medium; wherein the concentration ratio of said first solution to said second solution is from about 1:2 to about 2:1; and wherein the pH of said single composition is alkaline.

9. The composition of claim 8 wherein the pH is from about 9 to about 13.

10. The composition of claim 9 wherein the oxidant is selected from the group consisting of hydrogen peroxide, persulfate, perborate, urea peroxide and/or mixtures thereof.

11. The composition of claim 8 wherein the keratinous fibers are human hairs.

12. The composition of claim 9 wherein the oxidation dye further comprises, based on the total weight of the oxidation dye, about 90% to about 99.99% of a dye base, and about 0.01% to about 10.0% of said dye precursor.

13. The composition of claim 12 wherein the dye base is selected from the group consisting of water, ethanol, isopropanol, benzylalcohol, glycerol, glycols, glycol ethers, 2-butoxyethanol, ethylene glycol, ethylene glycol monoethyl ether, propylene glycol, diethyiene glycol monoethyl ether, oleic acid, surfactants, alkanoiamides, ammonia, erythorbic acid, EDTA and mircures thereof.

14. The composition of claim 9 wherein the iodide is potassium iodide.

* * * * *